(12) United States Patent
Van De Sluis et al.

(10) Patent No.: US 9,880,531 B2
(45) Date of Patent: Jan. 30, 2018

(54) ADAPTIVE CONTROL OF AMBIENCE SETTINGS

(71) Applicant: KONINKLIJKE PHILIPS N.V., Eindhoven (NL)

(72) Inventors: Bartel Marinue Van De Sluis, Eindhoven (NL); Roel Peter Geert Cuppen, Eindhoven (NL); Ingrid Christina Maria Flinsenberg, Eindhoven (NL); Evert Jan Van Loenen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 841 days.

(21) Appl. No.: 14/349,935

(22) PCT Filed: Oct. 2, 2012

(86) PCT No.: PCT/IB2012/055269
§ 371 (c)(1),
(2) Date: Apr. 4, 2014

(87) PCT Pub. No.: WO2013/050925
PCT Pub. Date: Apr. 11, 2013

(65) Prior Publication Data
US 2014/0257573 A1    Sep. 11, 2014

Related U.S. Application Data

(60) Provisional application No. 61/544,314, filed on Oct. 7, 2011.

(51) Int. Cl.
G05B 15/02    (2006.01)
H05B 37/02    (2006.01)
G06F 19/00    (2011.01)

(52) U.S. Cl.
CPC ......... G05B 15/02 (2013.01); G06F 19/3481 (2013.01); H05B 37/029 (2013.01);
(Continued)

(58) Field of Classification Search
CPC . G06F 19/3481; G05B 15/02; H05B 37/8221; H05B 37/0281; H05B 37/029; Y02B 20/42
See application file for complete search history.

(56) References Cited

U.S. PATENT DOCUMENTS 6,798,341 B1    9/2004  Eckel
2003/0100837 A1*  5/2003  Lys ..................... A61N 5/0616
                                                      600/476
(Continued)

FOREIGN PATENT DOCUMENTS

WO    2008142644 A1    11/2008
WO    2009090600 A1    7/2009
WO    2010079388 A1    7/2010

Primary Examiner — Charles E Anya

(57) ABSTRACT

The invention relates to a method and to an apparatus that enables the ambience of e.g. hospital rooms to adapt according the scheduled or non-scheduled activities throughout the day. The ambience generated by lights, sound devices, image, movie displays and other devices is controlled by an ambience controller (100) in dependence of day phases defined by a patient's day schedule or in dependence of other non-scheduled phases which may have been initiated in dependence of a trigger signal (215, 216) generated in response to activities such as the entering of a caterer.

16 Claims, 5 Drawing Sheets

(52) U.S. Cl.
CPC ..... *H05B 37/0227* (2013.01); *H05B 37/0281* (2013.01); *Y02B 20/42* (2013.01)

(56) References Cited

U.S. PATENT DOCUMENTS

| | | | |
|---|---|---|---|
| 2003/0227439 A1* | 12/2003 | Lee | G06K 9/00221 345/156 |
| 2004/0174326 A1* | 9/2004 | Yamamoto | H05B 37/0254 345/82 |
| 2005/0090915 A1* | 4/2005 | Geiwitz | G05B 15/02 700/90 |
| 2005/0108091 A1* | 5/2005 | Sotak | G06Q 30/0264 705/14.61 |
| 2007/0194939 A1* | 8/2007 | Alvarez | A61B 5/0002 340/573.1 |
| 2009/0065596 A1* | 3/2009 | Seem | F24F 11/0009 236/51 |
| 2009/0243517 A1 | 10/2009 | Verfuerth | |
| 2010/0277333 A1 | 11/2010 | Van De Sluis | |
| 2011/0022396 A1 | 1/2011 | Van De Sluis | |
| 2011/0137757 A1* | 6/2011 | Paolini | G06Q 30/0641 705/27.1 |
| 2011/0231320 A1* | 9/2011 | Irving | G06Q 30/00 705/80 |
| 2012/0323592 A1* | 12/2012 | Bechtel | G06Q 10/06 705/2 |
| 2013/0085615 A1* | 4/2013 | Barker | A61G 10/00 700/277 |
| 2013/0119891 A1* | 5/2013 | Herremans | H05B 33/0857 315/293 |

\* cited by examiner

ADAPTIVE CONTROL OF AMBIENCE SETTINGS

CROSS-REFERENCE TO PRIOR APPLICATIONS

This application is the U.S. National Phase application under 35 U.S.C. § 371 of International Application No. PCT/IB2012/055269, filed on Oct. 2, 2012, which claims the benefit of U.S. Provisional Patent Application No. 61/544,314, filed on Oct. 7, 2011. These applications are hereby incorporated by reference herein.

FIELD OF THE INVENTION

The invention relates to a method for controlling the ambience in a local environment of a caregiving facility such as a hospital.

BACKGROUND OF THE INVENTION

A patient in a hospital room is exposed to different activities during a day, for example meals, examinations, medicine intake, washing, etc. Normally, the ambience of the room remains unchanged during the day or possibly light settings may be changed manually.

In order to create the best healing ambience for the patient the ambience settings may be adjusted according to the activities, e.g. a low light intensity may be set during resting periods. However, the ambience settings should also be optimized to support the workflow for the hospital staff.

Accordingly, it is a problem that the ambience settings are not always optimal for the patient or the staff. Also, it may be a problem that the ambience settings are not always optimal for the healing of the patient, e.g. because the patient is not capable of finding a pleasant ambience setting.

Accordingly, there is a need to enable adapting the ambience settings to current needs.

WO 2009090600 discloses automatic creation of an atmosphere such as a lighting atmosphere combined with music, which is suited to social setting and mood in an environment such as a room. An embodiment of the invention provides a system for automatically creating an atmosphere suited to social setting and mood in an environment, comprising a sound receiving unit being adapted for receiving sound from the environment and generating an audio signal representing the received sound, an audio signal processing unit being adapted for receiving and analyzing the audio signal for social setting and mood in the environment, and an atmosphere creation unit being adapted for automatically generating control signals for an atmosphere creation system for creating an atmosphere based on the result; of the analysis of the audio signal. This system allows a comfortable and automatic creation of an atmosphere, which is suited to social setting and mood in an environment, for example in a room.

The inventor of the present invention has appreciated that an improved system for control of ambience settings is of benefit, and has in consequence devised the present invention.

SUMMARY OF THE INVENTION

It would be advantageous to achieve improvements within ambience control in hospital rooms or other local environments of caregiving facilities. It would also be desirable to enable utilization of e.g. patient schedules for adapting the ambience in e.g. a hospital room to a given phase the schedule. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention an ambience controller for controlling an ambience in a local environment of a caregiving facility in dependence of a schedule defining different phases during a period of time for a patient is presented that comprises:

a processor for determining if one of the phases of the schedule should be initiated or ended, and for determining an ambient parameter for control of the ambience in dependence of the phase to be initiated or ended.

Since the control of the ambience, e.g. control of ambient settings of an ambient device, may be performed in dependence of phases of a schedule such as a day schedule, the ambience may be optimally and automatically adapted to the needs of e.g. a patient or clinical staff. Such schedules may exist for other purposes, but may be exploited for adaptive control of the ambience.

The ambient parameters may be determined in dependence of start or end times of the phases of the schedule and/or in dependence of event triggers such as trigger signals from sensors located near the local environment.

In an embodiment the initiation or ending of one of the phases is determined in dependence of a trigger signal generated in dependence of an event. By use of triggers signals, phases of the schedule may be initiated or ended at other times than specified by the schedule, or non-scheduled phases may be initiated, to enable an improved adaptation of the ambience to different activities.

An event may comprise a scheduled time initiation or ending of one of the phases of the schedule, an elapse of a predetermined time period or a physical change in an environment of the caregiving facility which is measureable by a sensor. Accordingly, a trigger signal may be generated from the processing of the patient's own schedule, from other schedules, from a timer, from sensors or from other devices or processes.

It is understood that the ambience controller is configured for controlling an ambience device or different ambient devices capable of modifying the ambience in the local environment.

In an embodiment the processor is further configured for determining if a non-scheduled phase should be initiated in dependence of the trigger signal. The possibility of enabling non-scheduled phases to be initiated may enable a more flexible adaptation of the ambience since the ambience may be optimally adapted for non-scheduled activities.

In an embodiment the processor is further configured for determining if one of the phases of the schedule should be initiated or ended in dependence of a prioritization of multiple trigger signals generated in dependence of a multiple different events.

In an embodiment the processor is further configured for determining if one of the phases of the schedule should be initiated or ended in dependence of an order of multiple trigger signals generated in dependence of a multiple different events.

A second aspect of the invention relates to an ambience controller system that comprises:

the ambience controller of the first aspect, a storage unit for storing the schedules which are retrievable by the ambience controller.

The storage unit may further be configured for storing a plurality of the ambient parameters which are retrievable by the ambience controller in dependence of the determined phase to be initiated or ended.

A third aspect of the invention relates to an ambient system that comprises:

the ambience controller of claim the first aspect, an ambient device for creating an ambience in the local environment in dependence of the determined ambient parameter.

A fourth aspect of the invention relates to a method for controlling an ambience in a local environment of a caregiving facility in dependence of a schedule defining different phases during a period of time for a patient, where method comprises:

determining if one of the phases of the schedule should be initiated or ended, and determining an ambient parameter in dependence of the phase to be initiated or ended.

In summary the invention relates to a method that enables the ambience of e.g. hospital rooms to adapt according to the scheduled or non-scheduled activities throughout the day. The ambience generated by lights, sound devices, image, movie displays and other devices is controlled by an ambience controller in dependence of day phases defined by a patient's day schedule or in dependence of other non-scheduled phases which may have been initiated in dependence of a trigger signal generated in response to activities such as the entering of a caterer.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
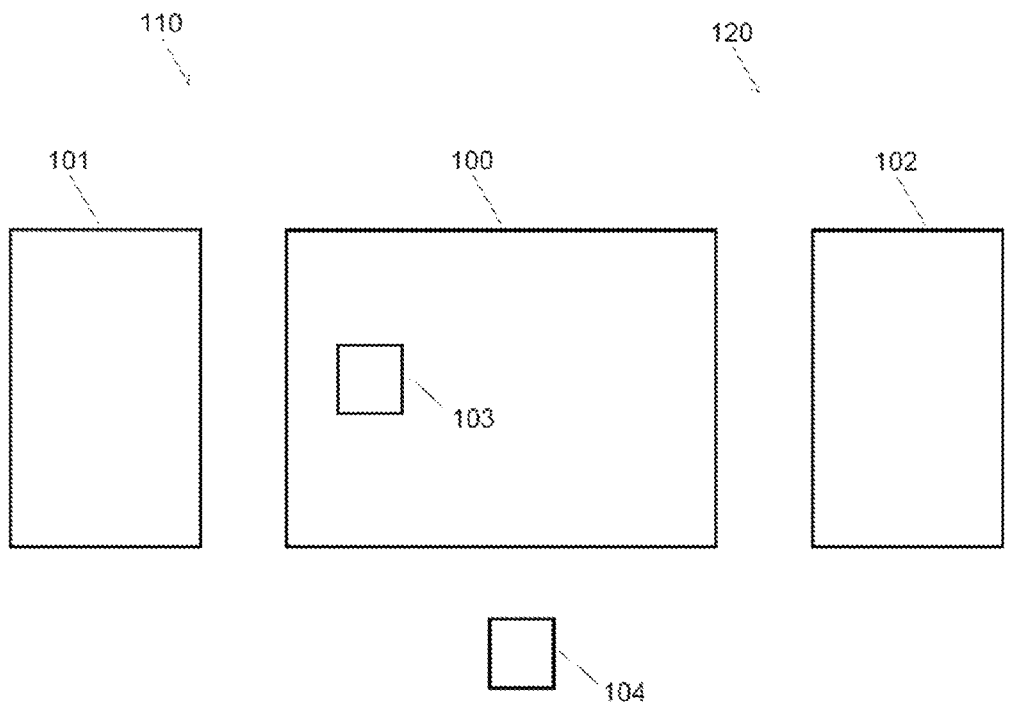
FIG. 1 shows an ambience controller 100 for controlling an ambience in a local environment of a caregiving facility.

FIG. 1 shows an ambience controller 100 for controlling an ambience in a local environment of a caregiving facility. The ambience controller may send a control signal with ambient parameters to an ambient device 102 for creating an ambience in the local environment in dependence of the ambient parameters. In order to adapt the ambience to the day structure of a patient the ambience is controlled in dependence of a schedule defining different phases during a period of time, e.g. a day, for a patient. The schedule of a patient as well as other patient schedules, staff schedule or other general schedules may be stored in a storage unit 101.

The ambience controller 100 and the storage unit 101 constitutes an ambience controller system 110, where the controller and the storage unit may be separate parts or integrated as a single device. The controller 100 may be constituted by two or more separate parts.

The ambience controller 100 and the ambient device 102 constitute an ambient system 120 which may additionally comprise the storage unit 101.

Herein a caregiving facility includes hospitals, nurseries, revalidation clinics and other facilities wherein patients or persons are located for some period of time for receiving care, nursing or supervision.

The ambience controller 100 comprises a processor 103 for determining if one of the phases of the schedule should be initiated or ended, and for determining the ambient parameter for controlling the ambience device 102. For example, the controller 100 may determine an ambience setting which is transmitted to the ambient device 102 for creating a specific setting of the ambience device.

Communication between the ambience controller 100, ambience devices 102, the storage unit 101 and other devices such as a sensor 104 may be performed wirelessly or by wired connections.

The table below shows an example of a schedule which defines different phases of a day for a patient, where as an example a wakeup phase may be defined between 7:30 and 8:00. The schedule may be a predefined general schedule or the schedule may be determined for a specific patient and for specific days.

| Phase | Start time | End time |
|---|---|---|
| sleep | 00:00 | 7:30 |
| wakeup | 7:30 | 8:00 |
| breakfast | 8:00 | 8:30 |
| morning | 8:30 | 11:30 |
| lunch | 11:30 | 12:00 |
| rest | 12:00 | 14:00 |
| wakeup | 14:00 | 15:00 |
| visitors | 15:00 | 17:00 |
| dinner | 17:00 | 18:00 |
| rest | 18:00 | 24:00 |

The initiation or ending of a phase of the schedule may be determined in dependence of the schedule, e.g. so that when the sleep phase ends at 7:30, the subsequent wakeup phase is initiated and a suitable ambient parameter is determined, e.g. so that lamps are controlled to generate a higher light intensity. A patient schedule or a phase thereof may be transmitted to the controller 100 so that the controller can process the time information of the schedule for determining if one of the phases of the schedule should be initiated or ended.

If the ambient parameter is determined in dependence of the ending of a phase, the subsequent phase is identified and an ambient parameter associated with this subsequent phase is determined so that the ambient parameter can be supplied to the ambient device. If the ambient parameter is determined in dependence of the initiation of a phase, the ambient parameter associated with this phase to be initiated.

Ambience devices 102 which are capable of modifying the ambience in the local environment in dependence of ambient parameters comprises lights, monitors, information screens, humidifiers, curtains, heating and cooling devices, ventilators, sound devices and other devices capable of modifying the visual or audible appearance, the climate, other physical parameters or the patient's perception of the local environment. For example, an information screen which display patient activities during a day such as the next meal and examination activities may be updated in dependence of a determined ambient parameter, i.e. a parameter which controls the screen to display the next two activities.

In order to enable a more adaptive initiation and ending of the phases of the schedule, the controller may be configured to determine the initiation or ending of a phase in dependence of a trigger signal generated in dependence of an event.

An event may be an elapse of a predetermined time period. For example, the breakfast phase may be ended after the elapse of a predetermined period. An event may also be a physical change in an environment of the caregiving facility which is measureable by a sensor. For example, the doctor's round phase may be initiated when a door switch detects the doctor's entrance onto the ward. An event may also be a scheduled time initiation or ending of one of a phase of a schedule, such as the patient's own schedule, cleaning personnel's schedule or other schedules.

Accordingly, a trigger signal may be generated from sensors 104, from a timer, from a processor which processes a schedule or from other devices. The controller 100 may have an input for receiving trigger signals generated by external devices and/or trigger signals may be generated by the controllers own processor 103.

Accordingly, the initiation or ending of a phase of the schedule may be determined in dependence of the start or end times of the schedule phases (e.g. start time=7:30 and end time=8:00 of the wake-up phase) and/or in dependence of event triggers.

The determination of an initiation or ending of a phase of the schedule may be the determination of an initiation or ending of a state defined by a computer program configured to be processed by the processor 103. Accordingly, the initiation or ending of a phase may simply be the initiation of a certain algorithm or setting of a variable of a computer program.

The determining an ambient parameter for control of the ambience in dependence of the determined phase may be performed e.g. by use of a look up table or an algorithm wherein different ambient parameters are associated with different phases. The look up table may be stored in a storage of the controller 100, stored in the storage unit 101 or some other storage. Alternatively, each phase is represented by a data record which contains ambient parameters which should be should be supplied to ambient devices 102 for generating an ambience according to this phase.

When a phase, i.e. the initiation or ending of a phase, is determined from a trigger signal, an ID number of the trigger signal may be compared with a list or a look up table wherein different ID numbers are associated with different phases. Again such a look up table may be stored in a storage of the controller 100, in the storage unit 101 or in some other storage. In case the trigger ID look up table is located in an external storage, the external storage receives the trigger ID and sends the phase which is associated with the ID back to the controller 100.

Since the day structure of a patient or other person need not be fully predetermined, but may also contain unexpected events, the processor 103 may be configured for determining if a non-scheduled phase should be initiated in dependence of a trigger signal. That is, some trigger signals may be generated in response to events which does not have a corresponding scheduled phase. For example, the schedule shown in the table above does not include a planned physical examination and, therefore, a non-scheduled examination phase may be triggered, e.g. by a sensor located near a patient room where the sensor is responsive to a doctor's personal ID card. A specific ambience may be created in response to the non-scheduled examination phase, e.g. an increased lighting intensity.

Since it may happen that different triggers for different phases are generated simultaneously or within a short period of time the processor 103 may be capable of handling such situations.

Thus, the processor 103 may be configured for determining if a non-scheduled phase or one of the phases of the schedule should be initiated or ended in dependence of a prioritization of multiple trigger signals generated in dependence of a multiple different events. For example, a trigger may be generated when a caterer enters a department and a trigger may be generated almost simultaneously in response to a doctor's intension to perform an examination. In this case the examination phase associated with the examination trigger may be more important than the lunch phase associated the caterer trigger and, therefore, an ambient parameter associated with the examination phase may be determined.

The prioritization may be determined in terms of predefined ranks of trigger signals, or in dependence of predefined ranks of phases of the schedule or of non-scheduled phases.

Alternatively or additionally, the processor may configured for determining if a non-scheduled phase or one of the phases of the schedule should be initiated or ended in dependence of an order of multiple trigger signals generated in dependence of a multiple different events. For example, a time trigger may be generated at 7:00 which initiates a wake-up phase and a subsequent breakfast trigger may be generated ten minutes later. Even though, the wake-up phase normally ends at 7:30, the breakfast trigger may initiate a new breakfast phase.

The table below shows an example of how different phases can be initiated or ended in response to different triggers.

| phase | Start trigger | End trigger |
| --- | --- | --- |
| wakeup | Time >7:00 & time <7:30 & sleep_state = awake | Caterer enters department OR caterer enters room OR time = 8:00 |
| meal | Caterer enters department OR caterer enters room | Duration_meal = 45 min |
| sleep | Lights are turned off & time >20:00 OR sleep_status = asleep & time >20:00 | Time = 7:30 |
| Nurse call | Call button pressed | Nurse call complete button pressed |

In order to avoid inappropriate initiation of a wake-up phase two events has to be fulfilled: the time has to be between 7:00 and 7:30 and it has to be detected that the patient is awake.

The sleep state may be detected by a sleep sensor which measures e.g. movements in the bed. The wake-up phase may be ended by a trigger generated in response to any of the events where the caterer enters the department or the room or that the time is 8:00. The meal phase is ended in response to the elapse of a fixed period of 45 minutes. The non-scheduled nurse call phase is initiated whenever a trigger signal is generated in response to pressing the call button in a hospital room and the nurse call phase is ended when a trigger signal is generated when the nurse presses the nurse call completion button.

Figure 2:
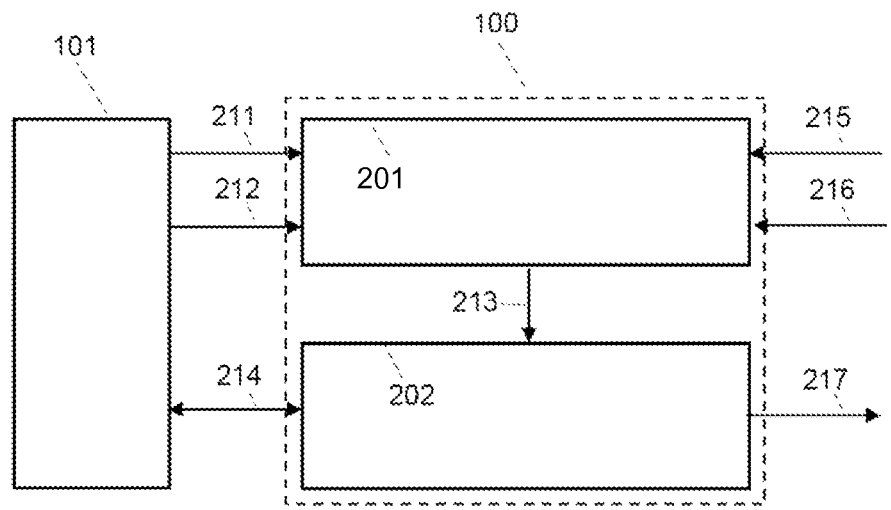
FIG. 2 shows another example of an ambience controller 100.

FIG. 2 shows a detailed example of possible system which comprises a storage unit 101 and an ambience controller 100 which is constituted by a phase unit 201 and an ambience unit 202. The phase unit 201 receives time based triggers via an input 215 and sensor triggers via an input 216. The ambience controller receives a schedule of planned phases and non-scheduled phases from the storage unit 101 in a step 211 and receives a trigger schema in a step 212. The trigger schema defines the relationship between phases of the schedule and different triggers. In a step 213 the initiation of a new phase has been determined in response to a start time of the scheduled phases or in response to an input trigger received via an input 215, 216. In step 214 an ID number of the phase to be initiated is transmitted to the storage unit 101 which sends an ambience ID number back to the ambience unit 202 which determines one or more ambient parameters from the ambience ID number and supplies the ambient parameters via an out 217 to one or more ambient devices. Alternatively, the ambient parameters may be supplied directly from the storage 101.

Figure 3:
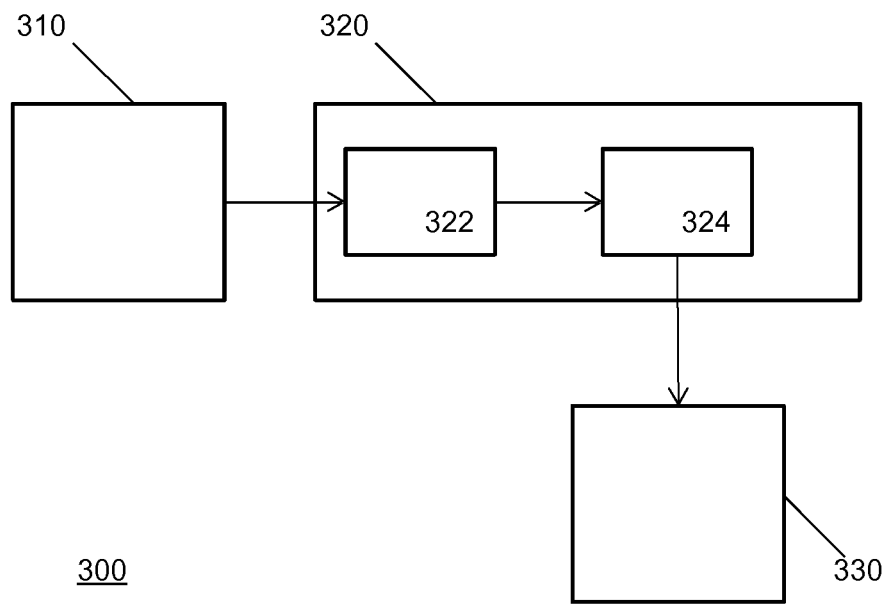
FIG. 3 shows an ambience system 330 in combination with a patient database 310.

FIG. 3 shows a system 300. One aspect when using an ambient system in practice is the need to have a phase schedule and optionally also a trigger schema which is defined throughout the day, preferably, for a full 24 hours per day. This could be arranged by having a staff member manually edit the schedules on a per-patient basis. However, the tedious nature of this chore and competition of higher priority care tasks may cause this to be neglected. In turn this may lead to a less than optimal use of the ambient system. For example, the ambient system may be programmed to the same schedule for multiple days and/or multiple patients. When used in this manner the beneficial effect of a daily ambient rhythm adapted to the activities of the patients is not fully reached. This problem has been solved by an ambiance scheduling system 320. It is noted that many care giving institutions already have a patient database; for example, hospitals frequently use a so-called hospital information system (HIS) or related scheduling system. From the patient database a patient agenda for a given patient and given date may be retrieved. Unfortunately, it has turned out not to be possible to use such a patient agenda directly as a phase schedule: the patient agenda typically does not contain ambient information, and moreover the patient agenda only covers a limited number of time-slots of the day. Obtaining a useful phase schedule, and optionally a trigger schema, may be done using an ambiance scheduling system 320, e.g., in a system such as system 300.

System 300 comprises a patient database 310, an ambiance scheduling system 320 and an ambient system 330.

Ambient system 330 may be an ambient system as described herein, e.g. ambient system 120. Ambient system 330 may comprise an ambience controller and an ambient device. Ambient system 330 receives the phase schedule from ambiance scheduling system 320. The phase schedule indicates how and when the ambience in e.g. a hospital room is to be adapted by the ambient device. A trigger schema may be used along with the phase schedule but this is not necessary. Ambient system may comprise a storage device of its own to store the phase schedule and trigger schema but instead may also rely on the ambiance scheduling system 320.

Ambiance scheduling system 320 receives a patient agenda from patient database 310. A patient agenda may comprise individual appointments for a patient. These appointments may be with a care giver, e.g., a doctor or other person. The appointment will typically indicate the location of the appointment so that it may be determined if the patient will be in his room or not. The patient agenda may also contain information about meal times, visit hours, activity hours, etc. Possibly, the information in the patient agenda may be collated from other sources, for example, mealtimes may be scheduled in a different system, but are nevertheless usually known the hospital information system.

The patient agenda is used by ambiance scheduling system 320 to produce a phase schedule for use by ambient system 330. There are two problems associated with patient agendas. First they do not contain ambient information and second they cover only part of the day. Ambiance scheduling system 320 automatically creates a day schedule for the ambient system based on the planned patient activities in the information system of the hospital. This process can be performed each day, say at a fixed time (e.g. at 0.00 h) in order to generate a proper dynamic atmosphere. The process may also be done multiple times per day, or performed whenever the patient agenda is updated.

Ambiance scheduling system 320 retrieves the patient agenda for a specific patient and specific date from the patient database, say, in the hospital information system (HIS) or related scheduling system by the day scheduler. The communication between the day scheduler and the HIS can be established by already existing standardized communication protocols, such as Health Level Seven International (HL7). For example, ambiance scheduling system 320 may communicate with patient database 310 using the HL7 messaging standards, such as HL7 v2.x or v3.0. Note that the use of this standardized protocol is convenient, but is not necessary. The patient agenda may also be communicated from patient database 310 to ambiance scheduling system 320 in the form of a data structure comprising time slots and corresponding activities, e.g. appointments etc.

Ambiance scheduling system 320 comprises an activity classifier 322. Classifier 322 classifies the activities in the patient agenda. For example, ambiance scheduling system 320 may have a table of a limited number of general activities on to which each specific activity in the patient agenda is mapped. For example, the activity table may contain only the 6 activities: meal, medical, visit, activities, rest, sleep. All appointments in the patient diary in which food is consumed are mapped onto meal, all appointments with doctors etc are mapped onto 'medical', all other active items are mapped to activities and all remaining non-sleep items are mapped onto rest. The in-principle the unlimited number of different entries that are possible in a patient agenda are thus significantly reduced. It is possible to have more or fewer than six types in the activity type table. The activity type table must contain at least two different activity types. Preferably, the activity type table has at least three different activity types; this makes it possible to distinguish between sleep, rest and active. Corresponding to the sleep, rest and active types, three ambiances of the three different intensities, e.g. light intensities, may be associated, ranging from (very) low to medium to high.

In a more refined embodiment, classifier 322 of ambiance scheduling system 320 classifies the activities from the patient agenda, such as e.g. clinical activity, social activity, care activity, food activity, therapy activity etc. These activities could also be classified based on their start and end time, such as "food activity in morning" (breakfast), "food activity in evening" (diner), etc. The classification could be based on a semantic analysis of the planned activities in the agenda, e.g. "Meeting with Doctor Smith" with meeting and doctor in the activity's description can be interpreted as a clinical activity, and "Therapy with physiotherapist Jones" with therapy in the activity's description can be interpreted as a therapy activity. Pre-agreed descriptions of planned activities could help in this part of the process. The classification could also be based on predefined tags that are added to the planned activities.

Classifier 322 may add default timeslots that often occur yet may not be present in the patient database. For example, classifier 322 may add a sleep timeslot and a wake-up timeslot. Classifier 322 may comprise the interface to receive the patient agenda from the patient database.

Ambience scheduling system 320 further comprises an ambience scheduler 324. Ambience scheduler associates ambient parameters to each classified timeslot of the patient agenda. For example, ambience scheduler 324 may associate a particular set of, possibly pre-determined, ambient parameters to a particular activity type.

For example, continuing the example given above, the ambiance scheduler 324 may associate the 'sleep' type with no, or nearly no, light. The 'rest' type may be associated with a soft and comforting atmosphere, e.g. with low, colored light. A 'medical' type may have uncolored (white) light to facilitate examination. Activities may also use uncolored light yet at a lowered intensity. In short to each of the classes an ambient atmosphere is associated that is designed to promote the corresponding activities.

Ambiance scheduling system 320 furthermore completes the patient agenda to a full phase schedule. For timeslots without a classified activity, ambiance scheduling system 320 fills in the schedule. There are various strategies that ambiance scheduling system 320 may follow to do these, some of which are detailed below.

For example, ambiance scheduler 324 of ambiance scheduling system 320 determines the type and timing of the ambience phases in the day schedule based on the timing of the classified patient activities.

Ambiance scheduling system 320 makes the phase schedule derived from a patient agenda available to the ambient system 330. Within the ambient system, e.g., an Ambience Service may generate the dynamic ambience for the patient based on this day schedule.

Figure 4:
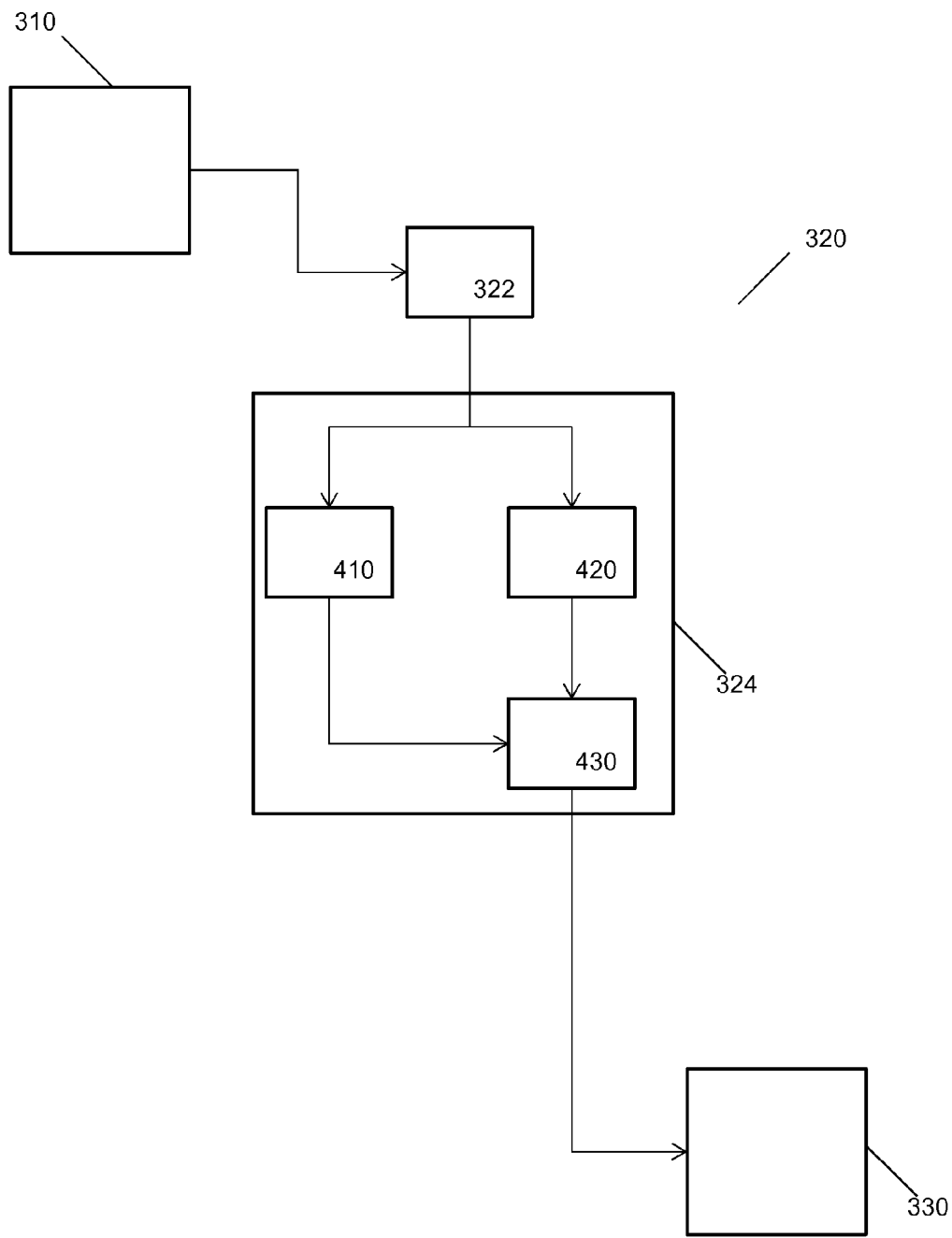
FIG. 4 illustrates an ambience scheduling system 320.

FIG. 4 illustrates one possible implementation of ambiance scheduling system 320, and in particular of ambiance scheduler 324. The ambiance scheduler 324 shown in FIG. 4 comprises an ambience class scheduler 410, an unclassified timeslot determiner 420 and an ambience non-class scheduler 430.

Ambience class scheduler 410 receives the classified patient agenda from classifier 322. Since patient activities are mapped to a limited set of activity types (or classes) these may be relatively straightforwardly be associated with ambience parameters. Also triggers may be associated in the same manner, e.g., to modify the moment of transition between phases depending on current circumstances instead of only on time. In practice triggers are very useful. For example, if a doctor arrives early or late at a bed side appointment, it is convenient to that the transition to medical ambiance is correspondingly early or delayed. However, for planning purposes, it is convenient to plan the day at least provisionally using time, since the occurrence of triggers is not known in advance. Whenever a phase change is discussed it is understood that a trigger may be associated with such a change to make the system dependent on actually occurring events.

For variety, the ambiance parameters may be varied somewhat, e.g., instead of associating a type with a single (set of) parameters, they may be chosen from a collection of such (sets of) parameters. The association between a timeslot and ambiance parameters may be done in various ways. For example, the ambiance parameters may be written in the agenda along with the timeslots. For example, the timeslots may have pointer information referring to ambiance parameters which are stored elsewhere.

Unclassified timeslot determiner 420 determines which timeslots have a well defined activity type and which timeslots do not. Often sequential timeslots for which an activity is planned in the patient database do not touch, i.e., the end-time of a first timeslot is not equal, but lies before, the start-time of a second timeslot. Unclassified timeslot determiner 420 determines where this is the case. In one implementation, unclassified timeslot determiner 420 defines new timeslots and assigns the class 'undefined' to them. Unclassified timeslot determiner 420 may be combined with classifier 322. A timeslot may be unclassified for two reasons, either the patient agenda did not have an entry for that time slot, or the classifier could not classify the entry. In a simpler embodiment, both types of time slots may simply be classified 'unclassified', it is also possible to have two unclassified types to keep the distinction. In such an embodiment, an unclassified timeslot which has a corresponding entry in the patient diary could be mapped to a default moderate active ambiance, possibly different from the 'rest' ambiance, whereas the unclassified timeslot which does not have a corresponding entry in the patent agenda could be filled using the mechanisms explained in FIG. 5a-5d (see below).

Ambiance scheduler 324 comprises an ambience non-class scheduler 430. Ambience non-class scheduler 430 associates ambience parameters to the timeslots identified by unclassified timeslot determiner 420 as unclassified by classifier 322. FIG. 5a-5d illustrates three ways in which the undefined timeslots may be filled with ambience information.

Figure 5A:
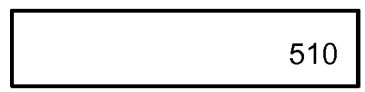
FIG. 5a-5d illustrates completion of phase schedules.
Figure 5A:
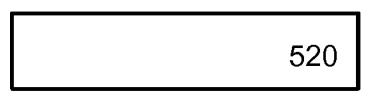

FIG. 5a shows the part of a classified patient agenda as ambience non-class scheduler 430 receives it from unclassified timeslot determiner 420. Time flows from the top of the page to the bottom, as indicated by the large arrow. FIG. 5a shows a first classified timeslot 510, and a second classified timeslot 520. The shown first timeslot ends before the second timeslot starts. For timeslots 510 and 520 appropriate ambience parameters are associated. In between timeslots 510 and 520 however is a timeslots which has not been classified.

Figure 5B:
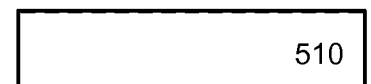
Figure 5B:

FIG. 5b shows a first way to resolve the unclassified timeslot. The end-time of the first timeslot 510 may be postponed and/or the start-time of second timeslot 520 may be bought forward. In this way the unclassified timeslot may be reduced in size, or removed completely. When the end-time of the first timeslot equals the start-time of the second timeslot, the ambience is defined for the entire time starting at the beginning of timeslot 510 and until the end of timeslot 520.

For example, suppose the first timeslot is classified as a 'clinical care phase' and the second timeslot as 'lunch' and that there are no activities planned in the time between, say from 11.30 h and 12.00 h. The ambience scheduler could then extend the clinical care phase from 11.30 h to 12.00 h or could start the lunch phase earlier at 11.30 h.

Figure 5C:
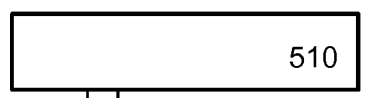
Figure 5C:
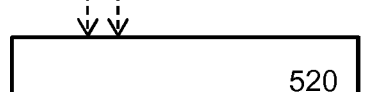

FIG. 5c shows a second way to resolve unclassified timeslots. During the time between the first and second timeslot the ambience parameters associated with the first timeslot are slowly changed towards the ambience parameters associated with the second timeslot. Changing ambient parameters may be done on a per parameter basis. For example, an ambient parameter, say controlling light intensity, may be changed from a level at the end of the first timeslot to the level at the beginning of the second timeslot. The changing may, e.g., be linear.

Figure 5D:
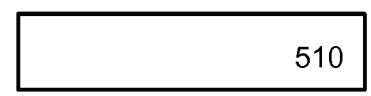
Figure 5D:

FIG. 5d shows yet another way to associate ambient information with unclassified timeslots. In FIG. 5d a new timeslot 525 is inserted between the first and second timeslot. The new timeslot 525 may be associated with a default class, say 'rest'.

Furthermore, the ways in which 5b, 5c and 5d resolve the situation of 5a may be combined. For example, it may be arranged that after applying 5b or 5d the time slots still do not touch each other. In that case the rest of the time may be filled with the rule of 5c.

Ambience non-class scheduler 430 may be programmed to apply these rules in different fashions.

The way an ambient parameter is assigned to an unclassified timeslot may be different for different ambient parameters. For example, a binary ambient parameter, which is either on or off is not, may not be slowly changed over time. For such a parameter it is preferable to use the system of 5b or 5d.

For example, ambience non-class scheduler 430 may have a first parameter and may be configured to apply 5b if the duration of the unclassified timeslot is less than a first parameter, this rule may be employed to remove the unclassified timeslot.

For example, ambience non-class scheduler 430 may in addition have a second parameter and may be configured to apply 5c if the duration of the unclassified timeslot is longer than the first parameter but less than the second parameter. In addition, one could configure ambience non-class scheduler 430 to apply 5d if the duration of the unclassified timeslot is longer than the second parameter.

Furthermore, one may configure ambience non-class scheduler 430 to increase the first parameter and apply 5b if the classes of first timeslot 510 and second timeslot 520 are the same. For example, if multiple clinical activities take place between e.g. 9.30 h and 11.30 h, then it may create one clinical care phase between 9.30 h and 11.30 h. Note that, this could differ with the clinical phase on another day in which less clinical activities are planned. Note that even the way in which unclassified timeslots are filled is thus adapted to the daily schedule.

Using a first and second parameter to determine how to fill in the unclassified timeslot between the first and second time slot has advantages. If the unclassified time is very short, i.e., shorter than the first parameter, there is not time enough to do a slow transition in a satisfying way. Thus it is better to quickly go from the ambient parameters associated to the first timeslot to those associated with the second timeslot. If there is more time, one may smoothly transition, this is the situation in which duration lies between the first and second parameters. However if a lot of time is available it is better to have a designed ambiance which has been optimized instead of a constantly changing one. For example, in a very long transition from rest to medical examination, say, one would spend a lot of time in an ambiance which is neither restful nor suitable for examination.

Example values are 10 seconds for the first parameter, and 10 minutes for the second parameters. However these parameters may be changed and optimized to fit a particular situation.

In other words, the ambience scheduler determines the transition between two successive ambience phases by filling in the non-defined time slots. These decisions could be based on a rule-based system available in a separate database within the day scheduler or the ambient system.

It has been found that a dynamic atmosphere throughout the day supports the daily rhythm of the patient. Where needed the atmosphere adapts to specific interrupts and visits, e.g. when doctor or cleaner is visiting. By using the ambient system, the negative effects of a rigid environmental condition are alleviated because the system provides a daily rhythm atmosphere in sync with, and optimized for, patient needs and the care agenda, and intelligently adapts to deviations thereof.

The system described in FIGS. 3-5, disclose a day scheduler that automatically creates a day schedule for an ambient system based on already existing and planned patient activities in the patient agenda of the hospital. Ultimately, by automating the creation of the day schedules, the ambient system does not need any interaction of staff members to generate a proper dynamic atmosphere that supports the daily rhythm of the patient. Based on a predefined set of rules undefined moments within a generated day schedule are automatically completed.

In an embodiment the system controls the ambience in a hospital room and has means to determine which patient(s) stay(s) in the hospital room (e.g. detecting patient ID badge, or retrieving a patient name from room planning system in the hospital information system).

As a possible extension the system may have presence detection in the room, or patient localization means in order to save energy and adapt the ambience on moments that the patient is out of the room for a longer period of time.

A patient localization system (say based on RFID badges) would also allow the ambience determined for that patient to follow him throughout the hospital.

Optionally the system comprises an electronic display that:
1) comprises means to associate the display with a patient or patient room (e.g.
detecting patient ID badge, or localization means to determine room number, than connecting to HIS to get patient ID);
2) presents a visual "patient agenda" overview to the associated patient showing scheduled activities;
3) shows scheduled ambiances for the scheduled activities, and comprises user interaction means for the patient to adjust properties of those scheduled ambiances (e.g. brightness, transitions, ambiance properties for a specific activity).

Ambiance scheduling system 320 has independent merit. For example, the ambiance scheduling system 320 may be embodied on a server. For example, the server may communicate with the patient database and the ambient system through an electronic messaging system, say a LAN, WLAN or the internet. For example, the ambiance scheduling system 320 could advantageously be operated as an online service; receiving patient agenda's over the web, and providing phase schedules. Communication with the server, especially when going over the internet is preferably in encrypted form.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ambience scheduling and controlling system comprising an ambience scheduling system and an ambience controller, wherein
the ambience controller is for controlling an ambience in a local environment of a caregiving facility in dependence of a schedule defining different phases during a period of time for a patient, where the ambience controller comprises:
a processor for determining if one of the phases of the schedule should be initiated or ended, and for determining at least one of a plurality of ambient parameters for control of the ambience in dependence of the phase to be initiated or ended, the ambience controller is configured to receive the schedule defining different phases from the ambience scheduling system, and wherein
the ambience scheduling system is configured to produce the schedule defining different phases, the ambience scheduling system comprising
a classifier comprising an interface configured to receive a patient agenda from a patient database, the patient agenda comprising a representation of timeslots and a corresponding patient activity for each timeslot, the classifier being configured to classify each patient activity as one of a plurality of activity types, and
an ambience scheduler, the ambience scheduler associating at least one of the plurality of ambient parameters to each classified activity corresponding to each timeslot of the patient agenda,
wherein the ambience scheduler comprises an unclassified timeslot determiner and an ambience non-class scheduler, the unclassified timeslot determiner being configured to determine timeslots in the patient agenda which are not classified, the ambience non-class scheduler being configured to associate at least one of the plurality of ambient parameters to each unclassified timeslot of the patient agenda,
wherein the ambience non-class scheduler is configured to detect a first classified timeslot and a second classified timeslot, a first and second ambient parameter being associated to the first and second classified timeslot respectively, an unclassified timeslot extending between the first and second classified timeslot, wherein the ambient parameter associated to the unclassified timeslot depends on the duration of the unclassified timeslot or at least one of the first and second ambient parameter.

2. The ambience scheduling and controlling system of claim 1 configured with a first and second parameter, the first parameter being less than the second parameter, wherein
the ambient parameter associated to the unclassified timeslot is the first or second ambient parameter, if the duration of the unclassified timeslot is less than the first parameter, and
a timeslot is inserted between the first and second timeslot having a default ambient parameter if the duration of the unclassified timeslot is more than the second parameter.

3. The ambience scheduling and controlling system of claim 1, wherein the initiation or ending of one of the phases is determined in dependence of a trigger signal generated in dependence of an event.

4. The ambience scheduling and controlling system of claim 3, wherein the event comprises a scheduled time initiation or ending of one of the phases of the schedule, an elapse of a predetermined time period or a physical change in an environment of the caregiving facility which is measureable by a sensor.

5. The ambience scheduling and controlling system of claim 3, wherein the processor is further configured for determining if a non-scheduled phase should be initiated in dependence of the trigger signal.

6. The ambience scheduling and controlling system of claim 3, wherein the processor is further configured for determining if one of the phases of the schedule should be initiated or ended in dependence of a prioritization of multiple trigger signals generated in dependence of multiple different events.

7. The ambience scheduling and controlling system of claim 3, wherein the processor is further configured for determining if one of the phases of the schedule should be initiated or ended in dependence of an order of multiple trigger signals generated in dependence of a multiple different events.

8. The ambience scheduling and controlling system of claim 1, wherein the ambience controller is configured for controlling an ambience device capable of modifying the ambience in the local environment.

9. The ambience scheduling and controlling system of claim 1, comprising
a storage unit for storing the schedules which are retrievable by the ambience controller.

10. The ambience scheduling and controlling system of claim 9, wherein the storage unit is further configured for storing a plurality of the ambient parameters which are retrievable by the ambience controller in dependence of the determined phase to be initiated or ended.

11. An ambient system, comprising:
the ambience scheduling and controlling system as in claim 1, and an ambient device for creating an ambience in the local environment in dependence of the determined ambient parameter.

12. A method for controlling an ambience in a local environment of a caregiving facility in dependence of a schedule defining different phases during a period of time for a patient, where method comprises:
determining if one of the phases of the schedule should be initiated or ended,
determining at least one of a plurality of ambient parameters in dependence of the phase to be initiated or ended,
receiving a patient agenda from a patient database, the patient agenda comprising a representation of timeslots and a corresponding patient activity for each timeslot,
classifying each patient activity as one of a plurality of activity types, associating at least one of the plurality of ambient parameters to each classified activity corresponding to each timeslot of the patient agenda,
determining timeslots in the patient agenda which are not classified, associating at least one of the plurality of ambient parameters to each unclassified timeslot of the patient agenda, detecting a first classified timeslot and a second classified timeslot, a first and second ambient parameter being associated to the first and second classified timeslot respectively, extending an unclassified timeslot between the first and second classified timeslot, wherein the ambient parameter associated to the unclassified timeslot depends on the duration of the unclassified timeslot or at least one of the first and second ambient parameter, and receiving the schedule defining different phases from an ambience scheduling system.

13. The method of claim 12, wherein the initiation or ending of one of the phases is determined in dependence of a trigger signal generated in dependence of an event.

14. The method of claim 13, wherein the event comprises a scheduled time initiation or ending of one of the phases of the schedule, an elapse of a predetermined time period or a physical change in an environment of the caregiving facility which is measureable by a sensor.

15. The method of claim 12, further comprising:
controlling an ambience device capable of modifying the ambience in the local environment.

16. The method of claim 13, further comprising:
determining if one of the phases of the schedule should be initiated or ended in dependence of an order of multiple trigger signals generated in dependence of a multiple different events.

* * * * *